(12) United States Patent  (10) Patent No.: US 7,450,229 B2
Ortyn et al.  (45) Date of Patent: Nov. 11, 2008

(54) METHODS FOR ANALYZING INTER-CELLULAR PHENOMENA

(75) Inventors: William E. Ortyn, Bainbridge Island, WA (US); David A. Basiji, Seattle, WA (US); David H. Lynch, Bainbridge Island, WA (US)

(73) Assignee: Amnis Corporation, Seattle, WA (US)

( * ) Notice: Subject to any disclaimer, the term of this patent is extended or adjusted under 35 U.S.C. 154(b) by 357 days.

(21) Appl. No.: 11/123,610

(22) Filed: May 4, 2005

(65) Prior Publication Data

US 2006/0068371 A1 Mar. 30, 2006

Related U.S. Application Data

(63) Continuation-in-part of application No. 10/628,662, filed on Jul. 28, 2003, now Pat. No. 6,975,400, which is a continuation of application No. 09/976,257, filed on Oct. 12, 2001, now Pat. No. 6,608,682, which is a continuation-in-part of application No. 09/820,434, filed on Mar. 29, 2001, now Pat. No. 6,473,176, which is a continuation-in-part of application No. 09/538,604, filed on Mar. 29, 2000, now Pat. No. 6,211,955, which is a continuation-in-part of application No. 09/490,478, filed on Jan. 24, 2000, now Pat. No. 6,249,341.

(60) Provisional application No. 60/567,911, filed on May 4, 2004, provisional application No. 60/240,125, filed on Oct. 12, 2000, provisional application No. 60/117,203, filed on Jan. 25, 1999.

(51) Int. Cl.
 *G01J 3/28* (2006.01)
 *G01J 3/51* (2006.01)

(52) U.S. Cl. .................. 356/326; 356/73; 356/419; 382/133

(58) Field of Classification Search ................. 382/128, 382/133
See application file for complete search history.

(56) References Cited

U.S. PATENT DOCUMENTS 3,922,069 A 11/1975 Kishikawa et al. .......... 359/633

(Continued)

FOREIGN PATENT DOCUMENTS

WO  WO 98/53093  11/1998

(Continued)

OTHER PUBLICATIONS

Kubota, Fumio et al. 1995. "Flow Cytometer and Imaging Device Used in Combination."*Cytometry*: 21:129-132.

(Continued)

*Primary Examiner*—F. L Evans
(74) *Attorney, Agent, or Firm*—Ronald M. Anderson

(57) ABSTRACT

Aspects of the present invention encompass the collection of multispectral images from a population of objects, and the analysis of the collected images to measure at least one characteristic of the population, using photometric and/or morphometric features identifiable in the collection of images. In an exemplary application, the objects are biological cells. In a particularly preferred, but not limiting implementation, the plurality of images for each individual object are collected simultaneously. In an empirical study, the characteristic being measured involves the synapse between conjugated cells. The conjugated cells may represent a subpopulation of the overall population of objects that were imaged. In a particularly preferred, yet not limiting embodiment, the present invention enables the quantization of the redistribution of cellular molecules due to the conjugation of different biological cells. Significantly, such quantization is not feasible with standard microscopy and flow cytometry.

19 Claims, 10 Drawing Sheets

U.S. PATENT DOCUMENTS

| | | | | |
|---|---|---|---|---|
| 4,635,293 | A | 1/1987 | Wantanabe | 382/130 |
| 4,677,680 | A | 6/1987 | Harima et al. | 382/112 |
| 4,770,992 | A | 9/1988 | Van den Engh et al. | 435/6 |
| 4,777,525 | A | 10/1988 | Preston, Jr. | 348/111 |
| 4,786,165 | A | 11/1988 | Yamamoto et al. | 356/23 |
| 5,096,807 | A | 3/1992 | Leaback | 435/6 |
| 5,141,609 | A | 8/1992 | Sweedler et al. | 356/344 |
| 5,153,916 | A | 10/1992 | Inagaki et al. | 382/151 |
| 5,159,397 | A | 10/1992 | Kosaka et al. | 356/73 |
| 5,159,398 | A | 10/1992 | Maekawa et al. | 356/73 |
| 5,159,642 | A | 10/1992 | Kosaka | 382/6 |
| 5,247,339 | A | 9/1993 | Ogino | 356/73 |
| 5,247,340 | A | 9/1993 | Ogino | 356/73 |
| 5,272,354 | A | 12/1993 | Kosaka | 250/574 |
| 5,351,311 | A | 9/1994 | Rogers | 382/156 |
| 5,422,712 | A | 6/1995 | Ogino | 356/73 |
| 5,444,527 | A | 8/1995 | Kosaka | 356/73 |
| 5,471,294 | A | 11/1995 | Ogino | 356/73 |
| 5,548,349 | A | 8/1996 | Mizuguchi et al. | 348/766 |
| 5,548,395 | A | 8/1996 | Kosaka | 356/73 |
| 5,568,315 | A | 10/1996 | Shuman | 359/487 |
| 5,596,401 | A | 1/1997 | Kusuzawa | 356/23 |
| 5,633,503 | A | 5/1997 | Kosaka | 250/458.1 |
| 5,644,388 | A | 7/1997 | Maekawa et al. | 356/73 |
| 5,674,743 | A | 10/1997 | Ulmer | 435/287.2 |
| 5,695,934 | A | 12/1997 | Brenner | 435/6 |
| 5,754,291 | A | 5/1998 | Kain | 356/344 |
| 5,760,899 | A | 6/1998 | Eismann | 356/326 |
| 5,764,792 | A * | 6/1998 | Kennealy | 382/133 |
| RE35,868 | E | 8/1998 | Kosaka | 250/574 |
| 5,831,723 | A | 11/1998 | Kubota et al. | 356/73 |
| 5,848,123 | A | 12/1998 | Strommer | 378/98.8 |
| 5,855,753 | A | 1/1999 | Trau et al. | 204/484 |
| 5,900,942 | A | 5/1999 | Spiering | 356/400 |
| 5,929,986 | A | 7/1999 | Slater et al. | 356/326 |
| 5,959,953 | A | 9/1999 | Alon | 369/44.41 |
| 6,007,994 | A | 12/1999 | Ward et al. | 435/6 |
| 6,014,468 | A | 1/2000 | McCarthy et al. | 382/254 |
| 6,066,459 | A | 5/2000 | Garini et al. | 435/6 |
| 6,116,739 | A | 9/2000 | Ishihara et al. | 353/31 |
| 6,156,465 | A | 12/2000 | Cao et al. | 430/30 |
| 6,210,973 | B1 | 4/2001 | Pettit | 436/172 |
| 6,211,955 | B1 | 4/2001 | Basiji et al. | 356/326 |
| 6,249,341 | B1 | 6/2001 | Basiji et al. | 356/73 |
| 6,256,096 | B1 | 7/2001 | Johnson | 356/335 |
| 6,259,807 | B1 * | 7/2001 | Ravkin | 382/133 |
| 6,330,081 | B1 | 12/2001 | Scholten | 358/463 |
| 6,330,361 | B1 | 12/2001 | Mitchell et al. | 382/211 |
| 6,381,363 | B1 | 4/2002 | Murching et al. | 382/164 |
| 6,522,781 | B1 | 2/2003 | Norikane et al. | 382/203 |
| 6,549,664 | B1 | 4/2003 | Daiber et al. | 382/232 |
| 6,620,591 | B1 | 9/2003 | Dunlay et al. | 435/7.2 |
| 6,763,149 | B2 | 7/2004 | Riley et al. | 382/294 |
| 7,006,710 | B2 | 2/2006 | Riley et al. | 382/294 |
| 2001/0006416 | A1 | 7/2001 | Johnson | 356/73 |
| 2001/0011018 | A1 | 8/2001 | Baum et al. | 455/439 |
| 2002/0030812 | A1 | 3/2002 | Ortyn et al. | 356/326 |
| 2002/0126275 | A1 | 9/2002 | Johnson | 356/317 |

FOREIGN PATENT DOCUMENTS

| | | |
|---|---|---|
| WO | WO 98/53300 | 11/1998 |
| WO | WO 99/24458 | 5/1999 |
| WO | WO 00/14545 | 3/2000 |
| WO | WO 00/42412 | 7/2000 |
| WO | WO 01/46675 | 6/2001 |
| WO | WO 02/17622 A | 2/2002 |

OTHER PUBLICATIONS

Kubota, F. 2003. "Analysis of red cell and platelet morphology using an imaging-combined flow cytometer." *Clin. Lab. Haem.*: 25:71-76.

Ong, Sim Heng. 1985. Development of a System for Imaging and Classifying Biological Cells in a Flow Cytometer. Doctor of Philosophy Thesis. University of Sydney, School of Electrical Engineering. (August).

Ong, S.H. et al. 1987. "Development of an Image Flow Cytometer." *Analytical and Quantitative Cytology and Histology. XIVth International Conference on Medical and Biological Engineering and the VIIth International Conference on Medical Physics*, Finland. (August): 375-382.

Ong, S.H. and P.M. Nickolls. 1991. "Optical Design in a Flow System For Imaging Cells." *Sciences in Medicine*: 14:2:74-80.

Ong, S.H. and P.M. Nickolls. 1994. "Analysis of MTF Degradation in the Imaging of Cells in a Flow System." *International Journal of Imaging Systems & Technology*: 5:243-250.

Satoh, Kaneo et al. 2002. "Small Aggregates of Platelets Can Be Detected Sensitively by a Flow Cytometer Equipped With an Imaging Device: Mechanisms of Epinephrine-Induced Aggregation and Antiplatelet Effects of Beraprost." *Cytometry*: 48:194-201.

Wang, Fu-sheng and Fumio Kubota. 2002. "A Novel Apoptosis Research Method With Imaging-Combined Flow Cytometer and HITC OR IR-125 Staining." *Cytometry*: 50:267-274.

Wietzorrek, Joachim et al. 1999. "A New Multiparameter Flow Cytometer: Optical and Electrical Cell Analysis in Combination With Video Microscopy in Flow." *Cytometry*: 35:291-301.

Hecht, Eugene. "Optics 4th ed." 2002. Addison-Wesley Longman, Inc., XP-002465391. ISBN: 0-8053-8566-5.

Gordy, Claire et al., "Visualization of antigen presentation by actin-mediated targeting of glycolipid-enriched membrane domains to the immune synapse of B cell APCs." Journal of Immunology, vol. 172, No. 4, Feb. 15, 2004. pp. 2030-2038, XP002481372 ISSN: 0022-1767.

* cited by examiner

METHODS FOR ANALYZING INTER-CELLULAR PHENOMENA

RELATED APPLICATIONS

This application is based on a prior copending provisional application Ser. No. 60/567,911, filed on May 4, 2004, the benefit of the filing date of which is hereby claimed under 35 U.S.C. § 119(e). This application is further a continuation-in-part application of a patent application Ser. No. 10/628,662, filed on Jul. 28, 2003, now U.S. Pat. No. 6,975,400 which is a continuation application of patent application Ser. No. 09/976,257, filed on Oct. 12, 2001, now U.S. Pat. No. 6,608,682 (issued Aug. 19, 2003), which is a continuation-in-part application of a patent application Ser. No. 09/820,434, filed on Mar. 29, 2001, now U.S. Pat. No. 6,473,176 which is a continuation-in-part application of patent application Ser. No. 09/538,604, filed on Mar. 29, 2000 now U.S. Pat. No. 6,211,955 (issued Apr. 3, 2001), which itself is a continuation-in-part application of patent application Ser. No. 09/490,478, filed on Jan. 24, 2000, now U.S. Pat. No. 6,249,341 (issued Jun. 19, 2001), which is a conventional application based on provisional application Ser. No. 60/117,203, filed on Jan. 25, 1999, the benefit of the filing dates of which is hereby claimed under 35 U.S.C. § 120 and 35 U.S.C. § 119(e). Copending patent application Ser. No. 09/967,257, noted above, is also based on provisional application Ser. No. 60/240,125, filed on filed Oct. 12, 2000, the benefit of the filing date of which is hereby claimed under 35 U.S.C. § 119(e).

FIELD OF THE INVENTION

The present invention relates generally to methods for detecting and quantifying molecules in, on, and between intact cells, and more specifically, to methods of analyzing the distribution of molecules effecting inter-cellular communication.

BACKGROUND OF THE INVENTION

Communication between cells of the immune system is integral to immune function. The process of T cell differentiation and maturation involves direct contact between dendritic cells and the maturing T cells, during which the T cells are selected for survival on the basis of their ability to recognize antigens associated with "self" without triggering an immune response, thereby preventing auto-immunity. Once mature, T cells frequently interact physically with antigen presenting cells, which expose the T cell to non-self antigens from bacteria, viruses, etc., ultimately triggering expansion of T cell populations that elicits a sustained immune response against the antigen source presented.

The study of inter-cellular communication is greatly facilitated by imagery of the cells in contact. Ideally, the imagery would be acquired from living cells; since it is likely that fixation of the cells would disrupt biochemical signaling mechanisms. Since the cells would be alive and therefore highly dynamic, it would be desirable to acquire multiple images of conjugated cells simultaneously. It would also be desirable to image the cells directly in fluid suspension, since immune cells are generally non-adherent and contact with a foreign surface could perturb the signaling process. Finally, it would be desirable to provide a sufficiently analytical throughput such that studies could employ the relatively rare primary T cell and antigen presenting cell conjugates obtained from whole blood, as opposed to model systems of cultured cells, to best model in vivo behavior.

Thus, there is a recognized need in the art for techniques that permit detection and quantization of cell conjugates in flow, which would provide an opportunity to study suspension-based cell lines and primary cells. Furthermore, methods for preparing cells in suspension for multi-spectral analysis are needed. The present invention meets such needs, and further provides other related advantages.

SUMMARY OF THE INVENTION

Aspects of the present invention relate to the collection of multispectral images from a population of objects, and the analysis of the collected images to measure at least one characteristic of the population, using photometric and/or morphometric features identifiable in the collection of images. In an exemplary application, the objects are biological cells. In a particularly preferred implementation, both photometric and morphometric features are used in the analysis. In a particularly preferred, but not limiting implementation, the plurality of images for each individual object are collected simultaneously.

To facilitate analysis, at least one aspect of the invention is directed to labeling at least a subset of the population of objects before using an imaging instrument to collect image data on the population of cells (or objects). In general, the present invention can be implemented using N−1 unique labels, where N is the number of different object types to be distinguished, as well as being implemented using as many labels as there are different object types, or even more labels than there are object types.

Exemplary steps that can be used to analyze objects such as biological cells in accord with an aspect of the present invention include collecting image data from a population of objects and identifying a subpopulation of objects from the image data for further analysis. In a particularly preferred, yet not limiting implementation, the objects are biological cells and the subpopulation corresponds to conjugated cells. Next, a particular feature of the objects in the subpopulation is identified for further study. The term feature is intended to refer to a particular structure, region, or portion of an object that can be readily discerned. For example, one analysis may focus on the nucleus or internal volume of each object in the subpopulation, while another analysis may focus on the cell membrane or outer boundary of each object in the subpopulation. In a particularly preferred aspect of the present invention, the feature selected for further study is the synapse between cell conjugates. For each object in the subpopulation, the feature selected for further study is identified. Using photometric and/or morphometric data from the collected images, at least one characteristic of the selected feature is measured.

Once a feature has been identified for analysis, the image data for the subpopulation can be manipulated using several different techniques. An exemplary technique is referred to as gating, a manipulation of data relating to photometric or morphometric imaging. A further exemplary technique is backgating, which involves further defining a subset of the gated data.

While not strictly required, preferably signal processing is performed on the collected image data to reduce crosstalk and enhance spatial resolution, particularly for image data collected using simultaneous multi-channel imaging.

In a particularly preferred, but not limiting implementation, the characteristic being measured involves the synapse between conjugated cells. The conjugated cells may represent a subpopulation of the overall population of objects that were imaged. In a particularly preferred, yet not limiting embodiment, the present invention enables the quantization of the redistribution of cellular molecules due to the conjugation of different biological cells. Significantly, such quantization is not feasible with standard microscopy and flow cytometry.

Analyzing the synapse between conjugated cells will facilitate the study of inter-cellular communication. In a preferred implementation of the present invention, the imagery collected from a population of biological cells includes collection of at least one of brightfield and darkfield imagery, and fluorescent imagery. In such an implementation, molecules suspected of playing a role in the communication pathway are fluorescently labeled, enabling changes in molecular quantities and molecular distributions as a result of the inter-cellular interaction to be detected. The collection of brightfield and/or darkfield imagery augments fluorescent labeling by eliminating the need for separate fluorescent identifying markers merely to distinguish the T cell from the antigen presenting cell, thereby allowing the use of more fluorescent probes for the simultaneous study of different molecules involved in the communication pathway. In one aspect of the present invention, the population of biological cells being imaged comprises relatively rare primary T cell and antigen presenting cell conjugates obtained from whole blood.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

Figure 3:
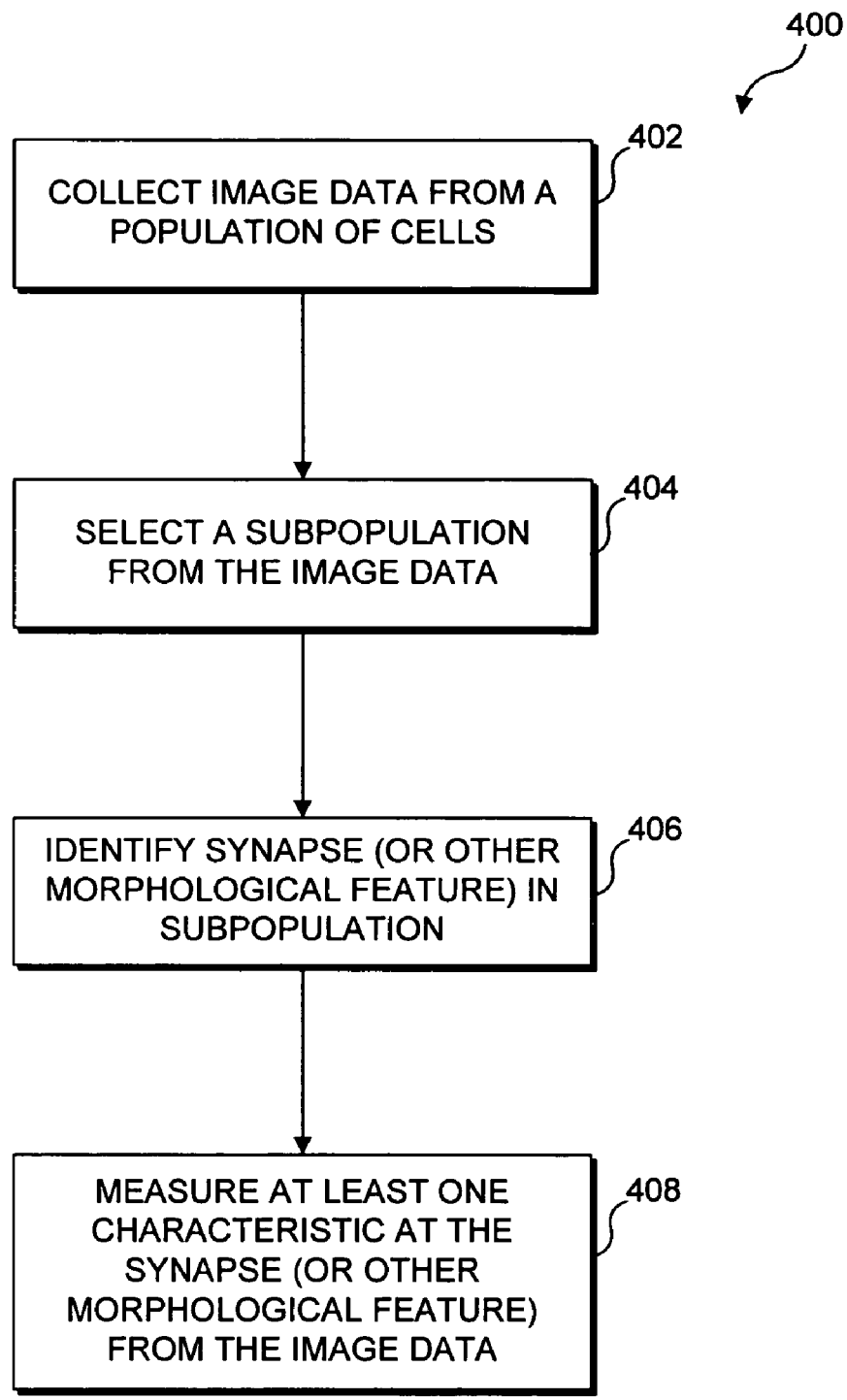
FIG. 3 is a flow chart of the overall method steps implemented in one aspect of the present invention.
Figure 11:
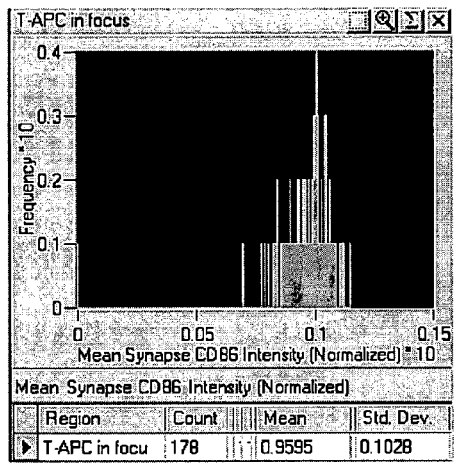
Figure 12:
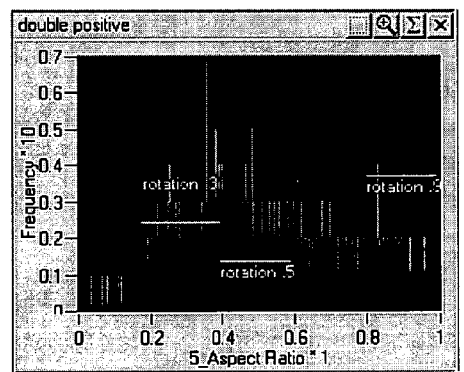
Figure 13:
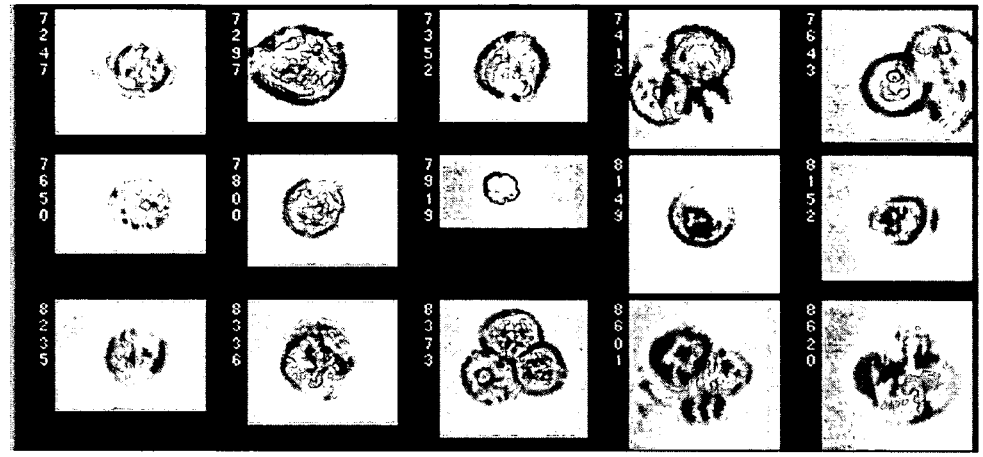
Figure 14:
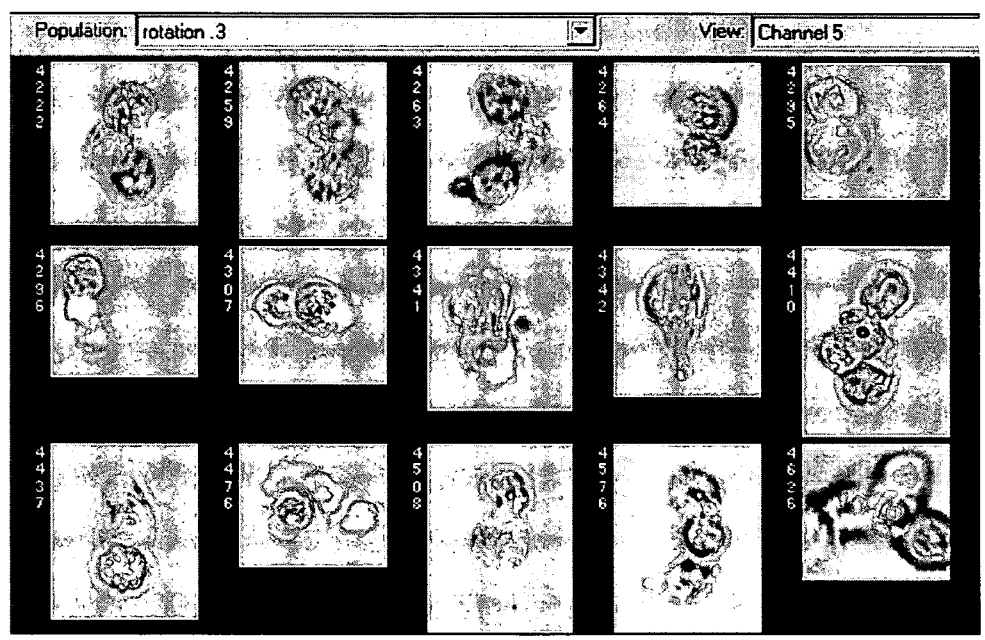
Figure 15:
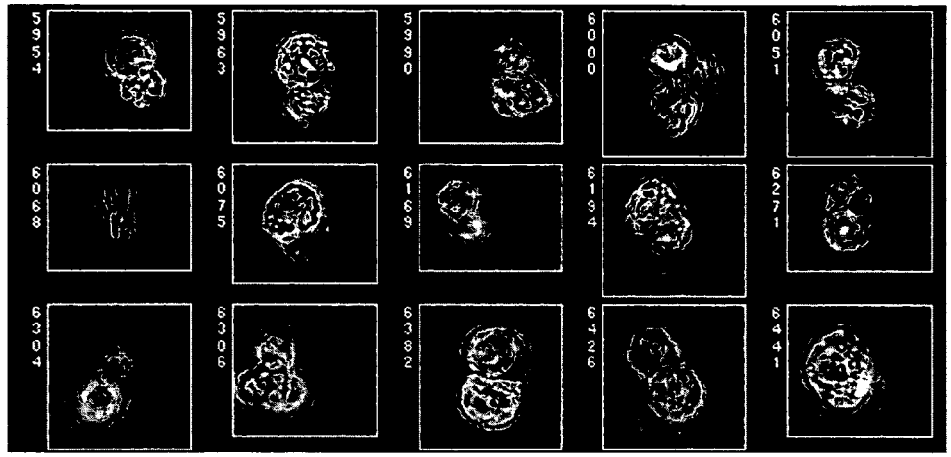
Figure 16:
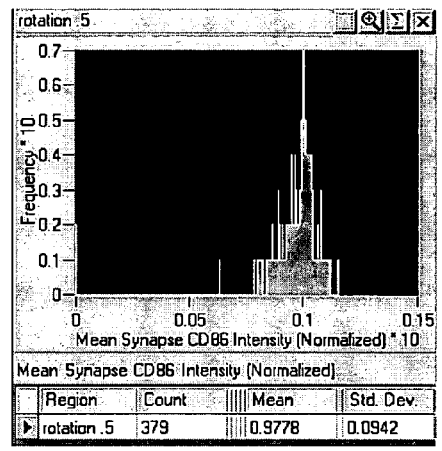
Figure 17:
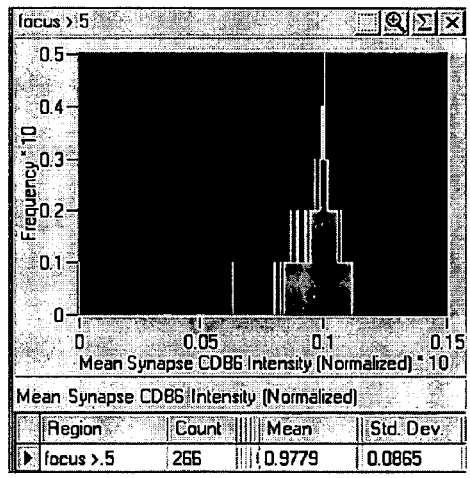
Figure 18:
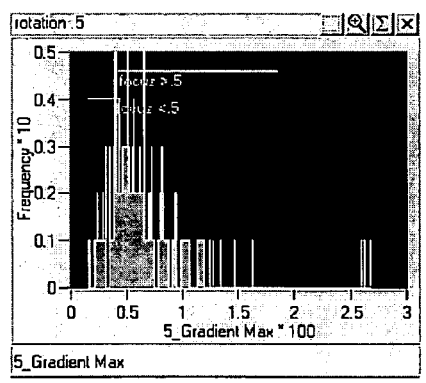
Figure 19:
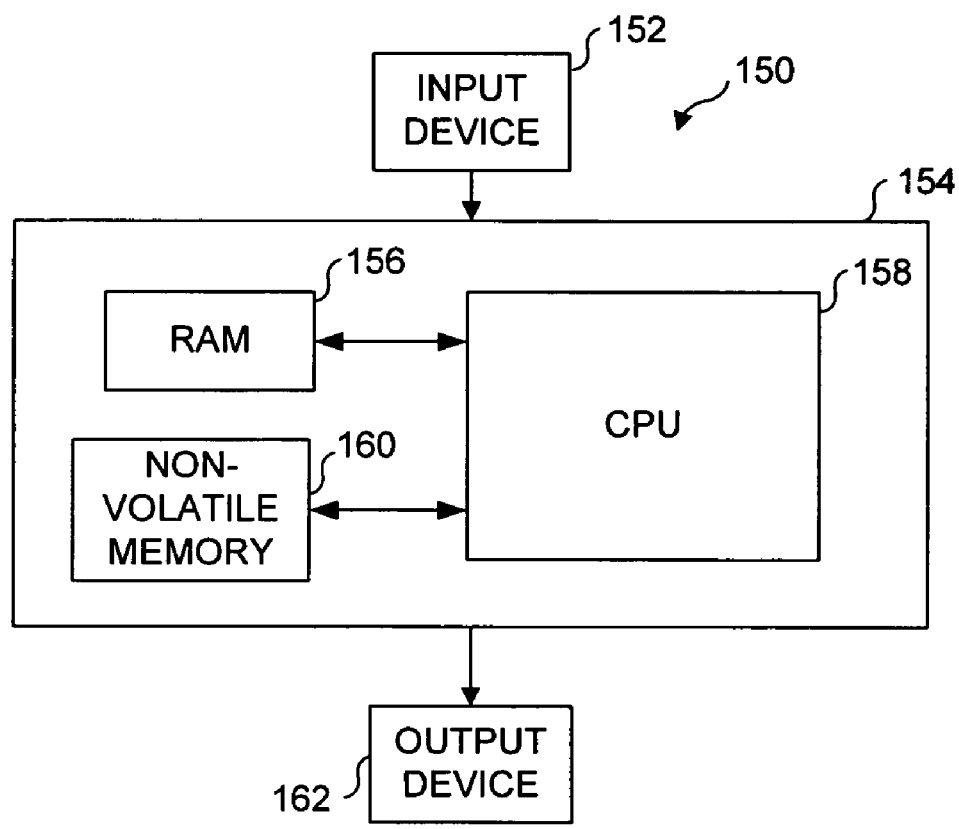

FIG. 11 graphically illustrates the frequency verses the mean synapse intensity of CD86 for a subpopulation analyzed according to the method steps of FIG. 3;

FIG. 12 graphically illustrates the frequency of a subpopulation of cell conjugates containing both T cells and antigen-presenting cells;

FIG. 13 includes images of cell conjugates with an aspect ratio of approximately 0.9;

FIG. 14 includes images of cell conjugates with an aspect ratio of approximately 0.3;

FIG. 15 shows images of cell conjugates with an aspect ratio of approximately 0.5;

FIG. 16 graphically illustrates frequency verses the mean synapse intensity of CD86 for conjugates with an aspect ratio approximating 0.5;

FIG. 17 graphically illustrates the frequency of cell conjugates considered to be in reasonably good focus;

FIG. 18 graphically illustrates frequency verses the normalized mean synapse intensity of CD86 for a subpopulation collected and analyzed according to the method steps of FIG. 3; and FIG. 19 schematically illustrates an exemplary computing system used to implement the method steps of FIG. 3.

DESCRIPTION OF THE PREFERRED EMBODIMENT

Overview

An aspect of the present invention relates to a system and method for imaging and analyzing conjugated biological cells entrained in a flow of fluid. In at least one embodiment, a plurality of images of biological cells are collected simultaneously; the plurality of images including at least two of the following types of images: a brightfield image, a darkfield image, and a fluorescent image. Images are collected for a population of biological cells (or objects with discernable morphological features). Once the imagery has been collected, the images can be processed to identify a subpopulation of images. The images in the subpopulation are processed to identify points of contact (i.e., synapses) between cell conjugates in the subpopulation. Further processing of the images in the subpopulation is performed to measure at least one characteristic at the identified synapses.

With respect to the following disclosure, and the claims that follow, it should be understood that the term population of objects refers to a group of objects including a plurality of objects. Thus, a population of objects must include more than one object.

A preferred imaging system to be used in collecting the image data required in the present invention will incorporate the following principal characteristics:
1. high speed measurement;
2. the ability to process very large or continuous samples;
3. high spectral resolution and bandwidth;
4. good spatial resolution;
5. high sensitivity; and
6. low measurement variation.

In particular, a recently developed imaging flow cytometer technology, termed ImageStream® (Amnis Corporation, Seattle Wash.) makes great strides in achieving each of the above noted principle characteristics. The ImageStream® instrument is a commercial embodiment of the flow imaging systems described above in detail with respect to FIGS. 1-19. These significant advancements in the art of flow cytometry are described in the following commonly assigned patents: U.S. Pat. No. 6,249,341, issued on Jun. 19, 2001 and entitled "Imaging And Analyzing Parameters of Small Moving Objects Such As Cells"; U.S. Pat. No. 6,211,955 issued on Apr. 3, 2001, also entitled "Imaging And Analyzing Parameters of Small Moving Objects Such As Cells"; U.S. Pat. No. 6,473,176, issued on Oct. 29, 2002, also entitled "Imaging And Analyzing Parameters of Small Moving Objects Such As Cells"; U.S. Pat. No. 6,583,865, issued on Jun. 24, 2003, entitled "Alternative Detector Configuration And Mode of Operation of A Time Delay Integration Particle Analyzer"; and U.S. patent application Ser. No. 09/989,031 entitled "Imaging And Analyzing Parameters of Small Moving Objects Such As Cells in Broad Flat Flow." While the ImageStream® platform represents a particularly preferred imaging instrument used to acquire the image data that will be processed in accord with the present invention, it should be understood that the present invention is not limited only to the use of that specific instrument.

As noted above, in addition to collecting image data from a population of biological cells, an aspect of the present invention involves processing the image data collected to measure at least one characteristic at a synapse between conjugated cells encompassed in the imaged population. A preferred image analysis software package is IDEAS® (Amnis Corporation, Seattle Wash.). The IDEAS® package evaluates nearly 200 features for every cell, including multiple morphologic and fluorescence intensity measurements, which can be used to define and characterize cell populations. The IDEAS® package enables the user to define biologically relevant cell subpopulations, and analyze subpopulations using standard cytometry analyses, such as gating and backgating. It should be understood, however, that other image analysis methods or software packages can be implemented in the present invention, and the preferred image analysis software package is intended to be exemplary, rather than limiting the invention.

Overview of a Preferred Imaging System

FIG. 1A is a schematic diagram of a preferred flow imaging system 510 (functionally descriptive of the ImageStream® platform) that uses TDI when capturing images of objects 502 (such as biological cells), entrained in a fluid flow 504. System 510 includes a velocity detecting subsystem that is used to synchronize a TDI imaging detector 508 with the flow of fluid through the system. Significantly, imaging system 510 is capable of simultaneously collecting a plurality of images of an object. A particularly preferred implementation of imaging system 510 is configured for multi-spectral imaging, and can operate with six spectral channels: DAPI fluorescence (400-460 nm), Darkfield (460-500 nm), FITC fluorescence (500-560 nm), PE fluorescence (560-595 nm), Brightfield (595-650 nm), and Deep Red (650-700 nm). The TDI detector can provide 10 bit digital resolution per pixel. The numeric aperture of the imaging system used with this invention is typically 0.75, with a pixel size of approximately 0.5 microns. However, those skilled in the art will recognize that this flow imaging system is neither limited to six spectral channels nor limited to either the stated aperture size or pixel size and resolution.

Moving objects 502 are illuminated using a light source 506. The light source may be a laser, a light emitting diode, a filament lamp, or a gas discharge arc lamp, and the system may include optical conditioning elements such as lenses, apertures, and filters that are employed to deliver broadband or one or more desired wavelengths or wavebands of light to the object with an intensity required for detection of the velocity and one or more other characteristics of the object. Light from the object is split into two light paths by a beam splitter 503. Light traveling along one of the light paths is directed to the velocity detector subsystem, and light traveling along the other light path is directed to TDI imaging detector 508. A plurality of lenses 507 are used to direct light along the paths in a desired direction, and to focus the light. While not shown, a filter or a set of filters can be included to deliver to the velocity detection subsystem and/or TDI imaging detector 508, only a narrow band of wavelengths of the light corresponding to, for example, the wavelengths emitted by fluorescent or phosphorescent molecules in/on the object, or light having the wavelength(s) provided by the light source 506, so that light from non-desired sources is substantially eliminated.

The velocity detector subsystem includes an optical grating 505a that modulates light from the object as a function of frequency, a light sensitive detector 505b (such as a photomultiplier tube or a solid-state photodetector), a signal conditioning unit 505c, a velocity computation unit 505d, and a timing control unit 505e that assures that TDI imaging detector 508 is synchronized to the flow of fluid 504 through the system. The optical grating preferably comprises a plurality of alternating transparent and opaque bars that modulate the light received from the object, producing modulated light having a frequency of modulation that corresponds to the velocity of the object from which the light was received. Preferably, the optical magnification and the ruling pitch of the optical grating are chosen such that the widths of the bars are approximately the size of the objects being illuminated. Thus, the light collected from cells or other objects is alternately blocked and transmitted through the ruling of the optical grating as the object traverses the interrogation region, i.e., the field of view. The modulated light is directed toward a light sensitive detector, producing a signal that can be analyzed by a processor to determine the velocity of the object. Thus, the velocity measurement subsystem is used to provide timing signals to TDI imaging detector 508.

Preferably, signal conditioning unit 505c comprises a programmable computing device, although an ASIC chip or a digital oscilloscope can also be used for this purpose. The frequency of the photodetector signal is measured, and the velocity of the object is computed as a function of that frequency. The velocity dependent signal is periodically delivered to a TDI detector timing control 505e to adjust the clock rate of TDI imaging detector 508. Those of ordinary skill in the art will recognize that the TDI detector clock rate is adjusted to match the velocity of the image of the object over the TDI detector to within a small tolerance selected to ensure that longitudinal image smearing in the output signal of the TDI detector is within acceptable limits. The velocity update rate must occur frequently enough to keep the clock frequency within the tolerance band as flow (object) velocity varies.

Beam splitter 503 has been employed to divert a portion of light from an object 502 to light sensitive detector 505b, and a portion of light from object 502a to TDI imaging detector 508. In the light path directed toward TDI imaging detector 508 there is a plurality of stacked dichroic filters 509, which separate light from object 502a into a plurality of wavelengths. Note that one of lenses 507 is used to form an image of object 502a on TDI imaging detector 508.

The theory of operation of a TDI detector, such as those employed in system 510, is as follows. As objects travel through a flow tube 511 (FIG. 1) and pass through the volume imaged by the TDI detector, light from the objects form images of the objects that travel across the face of the TDI detector. The TDI detector preferably comprises a charge coupled device (CCD) array, which is specially designed to allow charge to be transferred on each clock cycle in a row-by-row format, so that a given line of charge remains locked to or synchronized with a line in the image. The row of charge is clocked out of the array into a memory when it reaches the bottom of the array. The intensity of each line of the signal produced by the TDI detector corresponding to an image of an object is integrated over time as the image and corresponding resulting signal propagate over the CCD array. This technique greatly improves the signal-to-noise ratio of the TDI detector compared to non-integrating type detectors—a feature of great value when responding to images from low-level fluorescence emission of an object. Proper operation of the TDI detector requires that the charge signal be clocked across the CCD array in synchronization with the rate at which the image of the object moves across the CCD array. An accurate clock signal to facilitate this synchronization can be provided by determining the velocity of the object, and the present invention uses an accurate estimate of the object's velocity, and thus, of the velocity of the image as it moves over the CCD array of the TDI detector. A flow imaging system of this type is disclosed in commonly assigned U.S. Pat. No. 6,249, 341, the complete disclosure, specification, and drawings of which are hereby specifically incorporated herein by reference.

Figure 1:
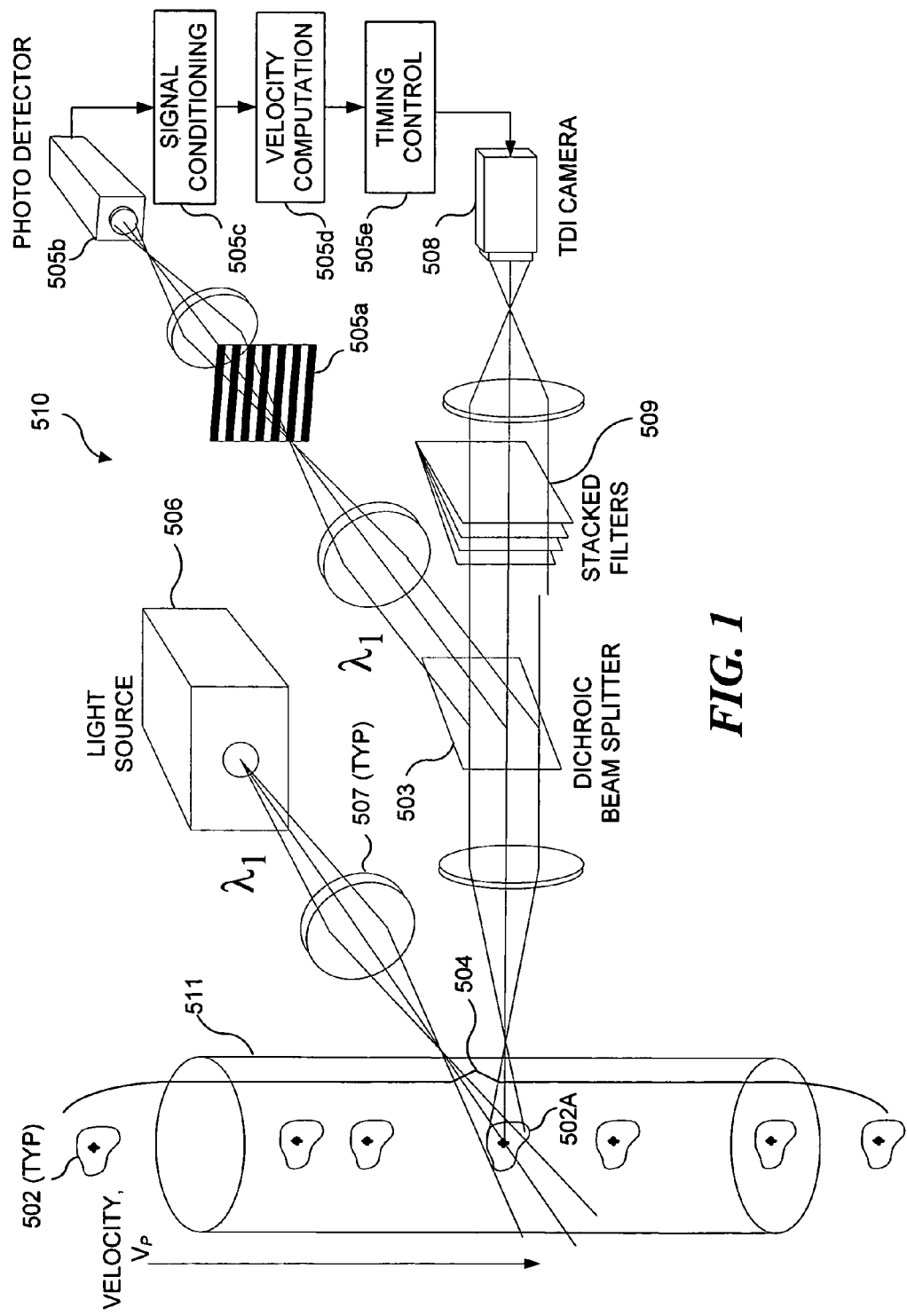
FIG. 1 is a schematic diagram of an exemplary flow imaging system that can be used to simultaneously collect a plurality of images from an object in flow.
Figure 2:
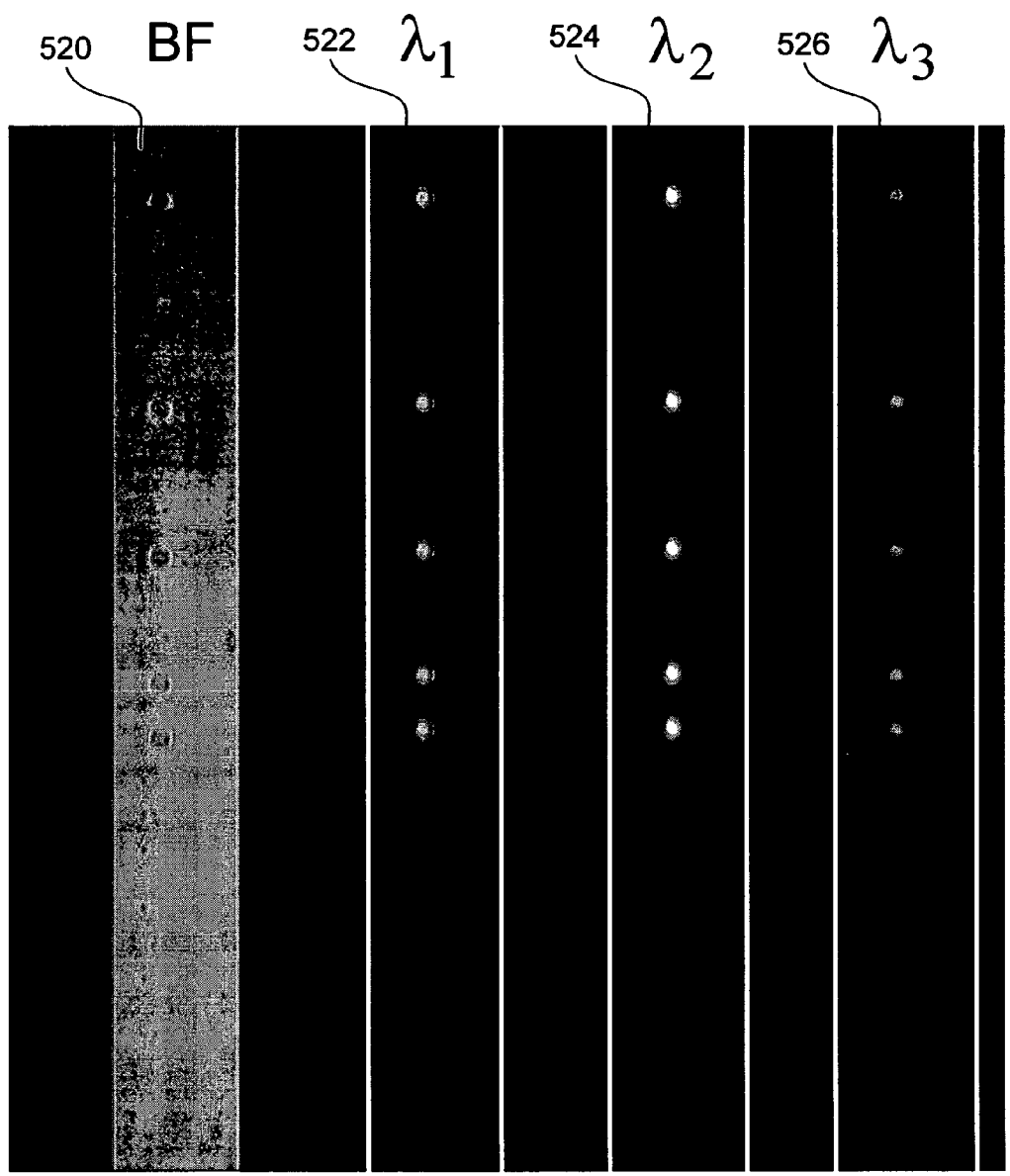
FIG. 2 is a pictorial representation of an image recorded by the flow imaging system of FIG. 1.

FIG. 2 is a pictorial representation of images produced by the flow imaging system of FIG. 1. A column 520, labeled "BF," includes images created by the absorption of light from light source 506 by spherical objects 502 entrained in fluid flow 504. The "BF" label refers to "brightfield," a term derived from a method for creating contrast in an image whereby light is passed through a region and the absorption of light by objects in the region produces dark areas in the image. The background field is thus bright, while the objects are dark. Thus, column 520 is the "brightfield channel." It should be understood that the inclusion of a brightfield image is exemplary, rather than limiting of the scope of the present invention. Preferably, the present invention utilizes a combination of brightfield images and fluorescent images, or darkfield images and fluorescent images.

The remaining three columns 522, 524, and 526 shown in FIG. 2 are respectively labeled "$\lambda 1$," "$\lambda 2$," and "$\lambda 3$." These columns include images produced using light that has been emitted by an object entrained in the fluid flow. Preferably, such light is emitted through the process of fluorescence (as opposed to images produced using reflected light). As those of ordinary skill in the art will recognize, fluorescence is the emission of light (or other electromagnetic radiation) by a substance that has been stimulated by the absorption of incident radiation. Generally, fluorescence persists only for as long as the stimulating radiation persists. Many substances (particularly fluorescent dyes) can be identified based on the spectrum of the light that is produced when they fluoresce. Columns 522, 524, and 526 are thus referred to as "fluorescence channels."

Additional exemplary flow imaging systems are disclosed in commonly assigned U.S. Pat. No. 6,211,955 and U.S. Pat. No. 6,608,682, the complete disclosure, specification, and drawings of which are hereby specifically incorporated herein by reference. The imaging systems described above in detail and incorporated herein by reference have considerable advantages over more conventional systems employed for the acquisition of images of biological cell populations. These advantages arise from the use in several of the imaging systems of an optical dispersion system, in combination with a TDI detector that produces an output signal in response to the images of cells and other objects that are directed onto the TDI detector. Significantly, multiple images of a single object can be collected at one time. The image of each object can be spectrally decomposed to discriminate object features by absorption, scatter, reflection or probe emissions using a common TDI detector for analysis. Other systems include a plurality of detectors, each dedicated to a single spectral channel.

These imaging systems can be employed to determine morphological, photometric, and spectral characteristics of cells and other objects by measuring optical signals including light scatter, reflection, absorption, fluorescence, phosphorescence, luminescence, etc. Morphological parameters include nuclear area, perimeter, texture or spatial frequency content, centroid position, shape (i.e., round, elliptical, barbell-shaped, etc.), volume, and ratios of any of these parameters. Similar parameters can also be determined for the cytoplasm of cells with the present invention. Photometric measurements with the invention enable the determination of nuclear optical density, cytoplasm optical density, background optical density, and the ratios of any of these values. An object being imaged with the present invention can either be stimulated into fluorescence or phosphorescence to emit light, or may be luminescent, producing light without stimulation. In each case, the light from the object is imaged on the TDI detector of the present invention to determine the presence and amplitude of the emitted light, the number of discrete positions in a cell or other object from which the light signal(s) originate(s), the relative placement of the signal sources, and the color (wavelength or waveband) of the light emitted at each position in the object.

An initial application of the imaging system comprising the present invention will likely be employed as a cell analyzer to determine one or more of the parameters listed above, for cells entrained in a fluid flowing through the imaging system. However, it should also be understood that this invention can be used for imaging other moving objects, where the objects have identifiable photometric and morphometric features.

Methods for Using a Multispectral Imaging System to Analyze Cell Structures/Synapses As noted above, aspects of the present invention involve both the collection of multispectral images from a population of biological cells, and the analysis of the collected images to measure at least one characteristic exhibited at a cellular feature, such as the synapse of conjugated cells identified from the multispectral images collected. Thus, an aspect of the present invention relates to the use of both photometric and morphometric features derived from multi-mode imagery of objects (e.g., cells) in flow to discriminate cell features in heterogeneous populations of cells, including in both non-adherent and adherent cell types. Discussed in more detail below are methods for analyzing cells in suspension or flow, such that cells tend to aggregate, which may be combined with comprehensive multispectral imaging to provide morphometric and photometric features to allow, for example, the quantization of the redistribution of cellular molecules not feasible with standard microscopy and flow cytometry.

As noted above, a preferred flow imaging system (e.g., the ImageStream® platform) can be used to simultaneously acquire multispectral images of cells in flow, to collect image data corresponding to brightfield, darkfield, and four channels of fluorescence. The ImageStream® platform is a commercial embodiment based on the imaging systems described in detail above. In general, cells are hydrodynamically focused into a core stream and orthogonally illuminated for both darkfield and fluorescence imaging. The cells are simultaneously trans-illuminated via a spectrally-limited source (e.g., filtered white light or a light emitting diode) for brightfield imaging. Light is collected from the cells with an imaging objective lens and is projected on a charge-coupled detector (CCD). The optical system has a numeric aperture of 0.75 and the CCD pixel size in object space is $0.5\mu^2$, allowing high resolution imaging at event rates of approximately 100 cells per second. Each pixel is digitized with 10 bits of intensity resolution, providing a minimum dynamic range of three decades per pixel. In practice, the spread of signals over multiple pixels results in an effective dynamic range that typically exceeds four decades per image. Additionally, the sensitivity of the CCD can be independently controlled for each multispectral image, resulting in a total of approximately six decades of dynamic range across all the images associated with an object. It should be understood that while the ImageStream® platform represents a particularly preferred flow imaging system for acquiring image data in accord with the present invention, the ImageStream® platform is intended to represent an exemplary imaging system, rather than limiting the invention. Any imaging instrument capable of collecting images of a population of biological cells sufficient to enable the image analysis described in greater detail below to be achieved, can be implemented in accord with the present invention.

Referring again to the preferred imaging system, the ImageStream® platform, prior to projection on the CCD, the light is passed through a spectral decomposition optical system that directs different spectral bands to different lateral positions across the detector (such spectral decomposition is discussed in detail above in connection with the description of the various preferred embodiments of imaging systems). With this technique, an image is optically decomposed into a set of a plurality of sub-images (preferably 6 sub-images; brightfield, darkfield, and 4 different fluorescent images), each corresponding to a different spectral (i.e., color) component and spatially isolated from the remaining sub-images. This process allows for identification and quantization of signals within the cell by physically separating on the detector, signals that may originate from overlapping regions of the cell. Spectral decomposition also allows multimode imaging: the simultaneous detection of brightfield, darkfield, and multiple colors of fluorescence. The process of spectral decomposition occurs during the image formation process, rather than via digital image processing of a conventional composite image.

The CCD may be operated using a technique called time-delay-integration (TDI), a specialized detector readout mode that preserves sensitivity and image quality even with fast relative movement between the detector and the objects being imaged. As with any CCD, image photons are converted to photo charges in an array of pixels. However, in TDI operation the photo charges are continuously shifted from pixel to pixel down the detector, parallel to the axis of flow. If the photo charge shift rate is synchronized with the velocity of the flowing cell's image, the effect is similar to physically panning a camera: image streaking is avoided despite signal integration times that are orders of magnitude longer than in conventional flow cytometry. For example, an instrument may operate at a continuous data rate of approximately 30 mega pixels per second and integrate signals from each object for 10 milliseconds, allowing the detection of even faint fluorescent probes within cell images that are acquired at relatively high speed. Careful attention to pump and fluidic system design to achieve highly laminar, non-pulsatile flow eliminates any cell rotation or lateral translation on the time scale of the imaging process (see, e.g., U.S. Pat. No. 6,532,061).

A real-time algorithm analyzes every pixel read from the CCD to detect the presence of object images and calculate a number of basic morphometric and photometric features, which can be used as criteria for data storage. Data files encompassing 10,000-20,000 cells are typically about 100 MB in size and, therefore, can be stored and analyzed using standard personal computers. The TDI readout process operates continuously without any "dead time", which means every cell can be imaged and the coincidental imaging of two or more cells at a time either in contact or not, presents no barrier to data acquisition.

Such an imaging system can be employed to determine morphological, photometric, and spectral characteristics of cells and other objects by measuring optical signals, including light scatter, reflection, absorption, fluorescence, phosphorescence, luminescence, etc. As used herein, morphological parameters may be basic (e.g., nuclear shape) or may be complex (e.g., identifying cytoplasm size as the difference between cell size and nuclear size). For example, morphological parameters may include nuclear area, perimeter, texture or spatial frequency content, centroid position, shape (i.e., round, elliptical, barbell-shaped, etc.), volume, and ratios of any of these parameters. Morphological parameters may also include cytoplasm size, texture or spatial frequency content, volume and the like, of cells. As used herein, photometric measurements with the aforementioned imaging system can enable the determination of nuclear optical density, cytoplasm optical density, background optical density, and the ratios of any of these values. An object being imaged can be stimulated into fluorescence or phosphorescence to emit light, or may be luminescent wherein light is produced without stimulation. In each case, the light from the object may be imaged on a TDI detector of the imaging system to determine the presence and amplitude of the emitted light, the number of discrete positions in a cell or other object from which the light signal(s) originate(s), the relative placement of the signal sources, and the color (wavelength or waveband) of the light emitted at each position in the object.

The present disclosure provides methods of using both photometric and morphometric features derived from multimode imagery of objects in flow. Such methods can be employed as a cell analyzer to determine one or more cell states or types, and cell features, in heterogeneous populations of cells when entrained in a fluid flowing through an imaging system. It should also be understood that these exemplary methods might be used for imaging and distinguishing other moving objects that have identifiable photometric and morphometric features. As used herein, gating refers to a subset of data relating to photometric or morphometric imaging. For example, a gate may be a numerical or graphical boundary of a subset of data that can be used to define the characteristics of particles to be further analyzed. Here, gates have been defined, for example, as a plot boundary that encompasses "in focus" cells, or sperm cells with tails, or sperm cells without tails, or cells other than sperm cells, or sperm cell aggregates, or cell debris. Further, backgating may be a subset of the subset data. For example, a forward scatter versus a side scatter plot in combination with a histogram from an additional marker may be used to backgate a subset of cells within the initial subset of cells.

In using an imaging system as described herein, it should be made clear that a separate light source is not required to produce an image of the object (cell), if the object is luminescent (i.e., if the object produces light). However, many of the applications of an imaging system as described herein will require that one or more light sources be used to provide light that is incident on the object being imaged. A person having ordinary skill in the art will know that the location of the light sources substantially affects the interaction of the incident light with the object and the kind of information that can be obtained from the images on a TDI detector.

In addition to imaging an object with the light that is incident on it, a light source can also be used to stimulate emission of light from the object. For example, a cell having been contacted with probe conjugated to a fluorochrome (e.g., such as FITC, PE, APC, Cy3, Cy5, or Cy5.5) will fluoresce when excited by light, producing a corresponding characteristic emission spectra from any excited fluorochrome probe that can be imaged on a TDI detector. Light sources may alternatively be used for causing the excitation of fluorochrome probes on an object, enabling a TDI detector to image fluorescent spots produced by the probes on the TDI detector at different locations as a result of the spectral dispersion of the light from the object that is provided by prism. The disposition of these fluorescent spots on the TDI detector surface will depend upon their emission spectra and their location in the object.

Each light source may produce light that can either be coherent, non-coherent, broadband or narrowband light, depending upon the application of the imaging system desired. Thus, a tungsten filament light source can be used for applications in which a narrowband light source is not required. For applications such as stimulating the emission of fluorescence from probes, narrowband laser light is preferred, since it also enables a spectrally decomposed, non-distorted image of the object to be produced from light scattered by the object. This scattered light image will be separately resolved from the fluorescent spots produced on a TDI detector, so long as the emission spectra of any of the spots are at different wavelengths than the wavelength of the laser light. The light source can be either of the continuous wave (CW) or pulsed type, and preferably is a pulsed laser. If a pulsed type illumination source is employed, the extended integration period associated with TDI detection can allow the integration of signals from multiple pulses. Furthermore, it is not necessary for the light to be pulsed in synchronization with the TDI detector.

In embodiments of the present invention, it is to be understood that relative movement exists between the object being imaged and the imaging system. In most cases, it will be more convenient to move the object than to move the imaging system. It is also contemplated that in some cases, the object may remain stationary and the imaging system move relative to it. As a further alternative, both the imaging system and the object may be in motion, which movement may be in different directions and/or at different rates.

Exemplary High Level Method Steps

FIG. 3 is a flow chart 400 schematically illustrating exemplary steps that can be used to analyze objects such as biological cells in accord with an aspect of the present invention. In a block 402, an imaging system, such as the exemplary imaging system described above in detail, is used to collect image data from a population of biological cells. In a block 404, a user identifies a subpopulation of images for further analysis. In the empirical study described below, image data corresponding to a subpopulation of conjugated cells (i.e., cells that were joined together) were selected for further analysis. In a block 406, a particular morphological feature exhibited in the subpopulation is selected for further analysis. In the empirical study, the synapse of the conjugated cells (i.e., the portion of the conjugated cells where the cells are joined together) was selected as the morphological feature for further analysis. In a block 408, image data corresponding to the selected morphological feature for the selected subpopulation of images is analyzed to identify at least one characteristic of the morphological feature.

Before using an imaging instrument to collect image data on the population of cells (or objects), it can be desirable to label one or more different types of objects, to facilitate later image analysis of the population. In the empirical study discussed in detail below, the overall population included two different types of biological cells, each of which was separately labeled. It should be understood however, that labeling each object to be imaged is exemplary, and not limiting on the invention. As will be discussed in greater detail below, the techniques of the present invention can be used to analyze image data to measure at least one characteristic of the synapse exhibited by conjugated cells, where only one of two different cell types are labeled. In general, the present invention can be implemented using N−1 unique probes, where N is the number of different cell types to be distinguished in the conjugates under study, as well as being implemented using as many probes as there are different cell types, or even more probes than there are cell types.

While not strictly required, in a working embodiment of the present invention additional processing was implemented to reduce crosstalk and spatial resolution for the multi-channel imaging. The crosstalk reduction processing implemented therein is described in commonly assigned U.S. Pat. No. 6,763,149, the specification, disclosure, and the drawings of which are hereby specifically incorporated by reference. Those of ordinary skill in the art will recognize other types of crosstalk reduction techniques could also be implemented.

Exemplary Cell Conjugate Analysis

Figure 4:
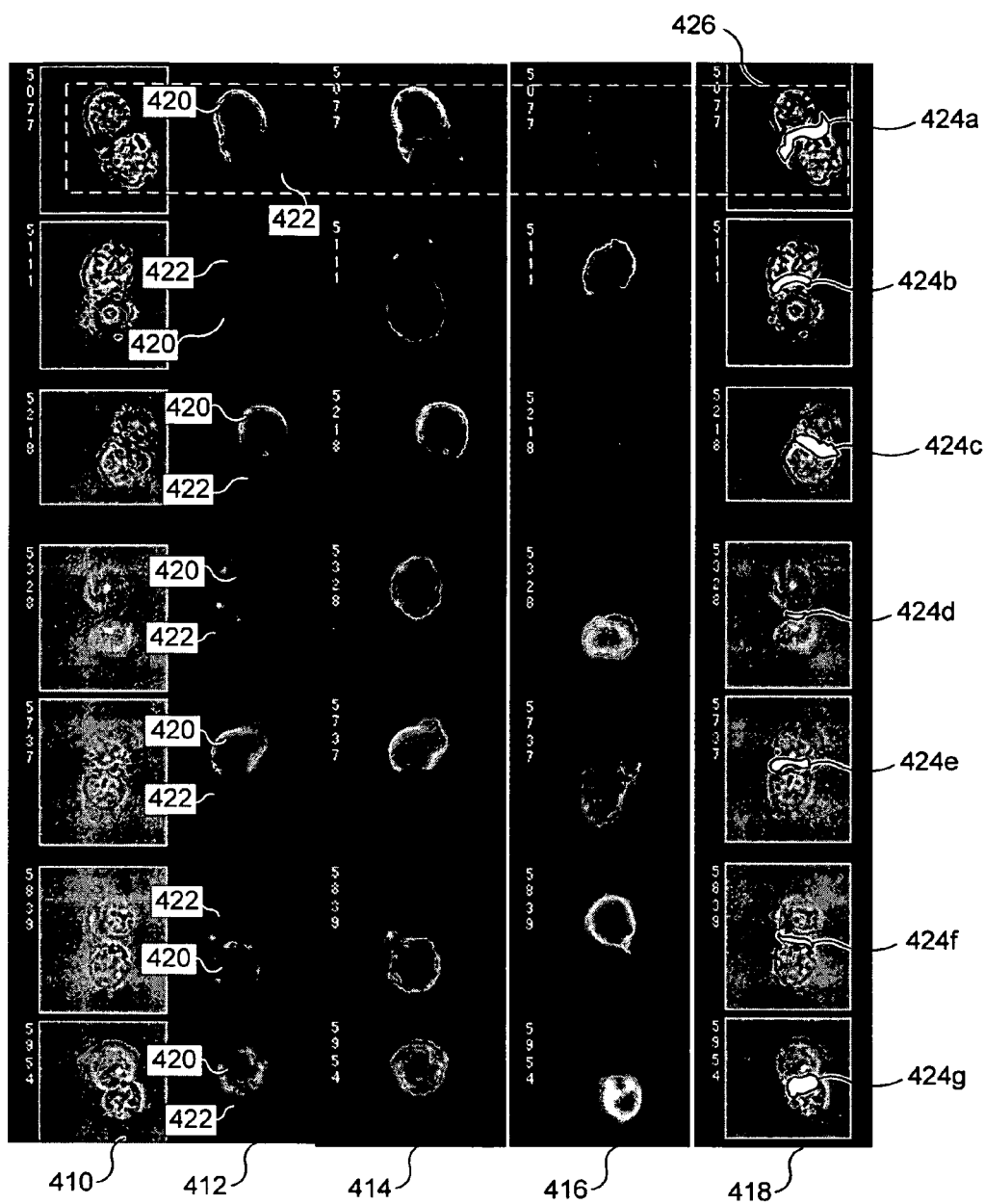
FIG. 4 is a composite image formed from exemplary image data collected using the flow imaging system of FIG. 1 and analyzed according to the method steps of FIG. 3.

FIG. 4 is a composite image formed from exemplary image data collected using an ImageStream® platform. As noted above, the ImageStream® platform is a commercial embodiment based on the flow imaging instrument discussed above in detail with respect to FIG. 1. Each of columns 410-418 corresponds to a different channel (i.e. a different spectral image) that was simultaneously collected. Thus, each image in a box 426 represents the same conjugate of two biological cells. Similarly, each other row represents the same object or objects. The image data was collected based on a population of more than 10,000 antigen-specific T cells and antigen pulsed antigen presenting cells. The T cells were stained with HLA (human leukocyte antigen)-FITC (fluorescein isothiocyanate), resulting in green stained T cells. The antigen presenting cells where stained with CD86-PE (phycoerythrin), resulting in red stained antigen presenting cells. Both the green stained T cells and the red stained antigen presenting cells were incubated together at 37° C. for 30 minutes, and thereafter introduced into an ImageStream® flow imaging instrument, such that a plurality of different spectral images of each cell were simultaneously collected as the cells passed through the flow imaging instrument. The image data for the population of stained T cells and stained antigen presenting cells were then evaluated using the IDEAS® software. As indicated above, the use of that particular software package is simply exemplary, and not intended to limit the invention. Those of ordinary skill in the art will recognize that other image analysis software packages are available.

After image data from the entire population of stained T cells and stained antigen presenting cells was collected (collection of image data corresponds to block 402 of FIG. 3), the resulting images were analyzed to identify a cell conjugate (i.e., combinations of cells corresponding to a green stained T cell joined with a red stained antigen presenting cell) subpopulation. Note that defining a subpopulation corresponds to block 404 of FIG. 3. Cell conjugates were identified as being objects staining positively for both FITC and Phycoerythrin (PE) stains. For the purposes of the empirical study, it was determined that the subpopulation should include only conjugates with limited numbers of cells (i.e., 2-3) per conjugate, although the technique being described herein is also applicable to conjugates containing larger numbers of cells. The subpopulation of cell conjugates was then further limited to include only cell conjugates including a limited number of cells, in which each of the cells were considered to be in the same focal plane. The process of defining the subpopulation is described in detail below. With respect to the empirical study, the image analysis software employed enabled two different mechanisms to be utilized to define the subpopulation, each of which are described below.

Before discussing the definition of the subpopulation further, it may be beneficial to describe FIG. 4 in greater detail. Column 410 includes brightfield images of cell conjugates. Each cell conjugate in column 410 clearly includes two cojoined cells. Column 412 is a color image, clearly indicating that each cell conjugate includes one green stained T cell 420 and one red stained antigen presenting cell 422. As will be described in greater detail below, each image in column 414 is based on the use of the mask to identify the T cell portion of the cell conjugate, and each image in column 416 is based on the use of the mask to identify the antigen presenting cell portion of the cell conjugate. Column 418 includes brightfield images of cell conjugates with the synapse portion of each cell conjugate highlighted by a mask 424a-424g. The image data encompassed by the masked synapses in the subpopulation can then be analyzed to identify at least one characteristic. The characteristic being measured in the exemplary study involving T cells and antigen presenting cells will be discussed in detail below.

The analysis performed in the exemplary study is based on first identifying cell clusters containing at least one T cell and one antigen presenting cell, narrowing in on clusters consisting of only a single T cell and a single antigen presenting cell (column 412), defining the region of contact (i.e., the synapse) between the two cells (column 418), and defining the region of each cell outside of the synapse (columns 414 and 416). Once the synaptic and extra-synaptic regions are defined for each cell conjugate, the mean intensity of the red signal, which is a probe specific for the cell surface marker CD 86, can be quantitated separately for the synaptic and extra-synaptic region of each antigen presenting cell. If the mean CD 86 intensity within the synapse is ratioed over the mean CD 86 intensity outside of the synapse, CD 86 migration to, or exclusion from, the synapse will be revealed as an increase or decrease of the ratio from unity, respectively.

Figure 5:
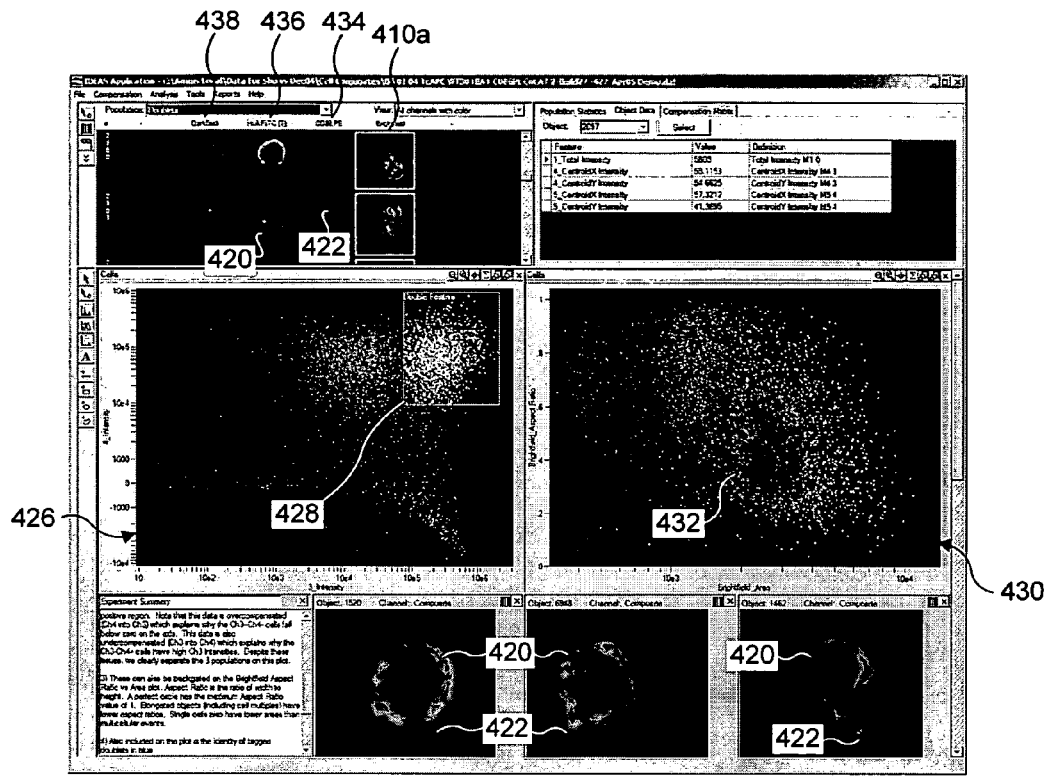
FIGS. 5-10 are exemplary graphical user interfaces used to implement the method steps of FIG. 3.

A dot plot 426 in the left portion of FIG. 5 (a screen shot from the exemplary imaging processing software) is a plot of green intensity (x-axis) versus red intensity (y-axis) for every object in the data file. Lone T cells are HLA-bright but CD86-dim, placing them in the lower right quadrant of the plot. Lone antigen presenting cells are HLA-dim but CD86-bright, placing them in the upper left quadrant of the plot. Conjugates including at least one T cell and one antigen presenting cell appear in the upper right quadrant of the plot. These double-positive cells are "gated" for subsequent analysis by drawing a rectangular region 428 around the dot cluster in the upper right of the plot. This gating technique is one example of selecting a subpopulation (the method step of block 404 in FIG. 3). Note that the screenshot of FIG. 5 includes brightfield images 410a, spectral images 434 corresponding to the CD 86 red stain, spectral images 436 corresponding to the FTIC green stain, and darkfield images 438.

The double-positive population gated in region 428 contains not only conjugates of one T cell with one antigen presenting cell, but likely also includes clusters of three or more cells, whose inclusion is undesirable (because the exemplary study intended to focus on simple conjugates including one antigen presenting cell and one T cell). A second scatter plot 430 in FIG. 5 illustrates the use of brightfield imagery to eliminate conjugates of more than two cells. All cells in the data file are plotted using brightfield area (x-axis) versus brightfield aspect ratio (y-axis). The double positive population is "back-gated" onto the plot by changing the symbol and color of each object that fell into the double-positive gate defined in the other dot plot. It is evident that the double-positive population tends to be larger and spans a wider range of aspect ratios than the single-positive population, which consists primarily of single cells. The subset of the double-positive objects that primarily includes conjugates of just two cells was selected using a rectangular gate 432. The boundaries of the gate were determined by defining a population of two-cell conjugates from the double-positive image gallery shown in the upper left of the figure and back-gating this population on the dot plot to determine the range of typical area and aspect ratio values for two-cell conjugates.

Alternatively, an operator can view the image data collected to visually identify one or more cell conjugates including one T cell and one antigen presenting cell, select that cell conjugate, and instruct the image analysis software to identify all other cell conjugates whose image data strongly correlates with the specific cell conjugate identified by the operator (using the gating and backgating techniques noted above).

In order to quantitate the intensity of molecular markers within the synaptic region (area of overlap or contact) relative to the regions outside of the synapse, it is first necessary to define the synapse. The region of overlap between the antigen presenting cell and the T cell can be defined in multiple ways. One method of defining the region of overlap is to generate a calculated image that is a transform of the signals in pixels at each location in the spectral images (for instance the product of the signals), such that overlapping regions exhibit greatly increased pixel values. A simple threshold function set at a level above the untransformed pixels in either spectral image will then preferentially select for pixels in the calculated image that are in common between the two spectral images. The pixel addresses in common can then be used to refer to the original signal levels for quantization both within and outside the synapse.

Another method is to employ binary masks, one per cell, that delineate the extent of each cell image. The extent of the mask is limited by the ability to detect image signals over the background level. Consider two spectral images of the same cell cluster, such as those shown in dot plot 426 of FIG. 4. If each cell is labeled with a different color (red/green in this case), the red and green spectral channels (columns 414 and 416) will each contain an image of only one of the cells. By extension, each image mask will correspond to only one cell. Since masks are binary, a Boolean AND operation using the (x,y) coordinates of the pixels comprising each mask will yield a new mask containing only those pixels in common between the two cell images (i.e. mask 424a). This methodology is extensible to conjugates of more than two cell types as long as each cell type bears a unique probe and the Boolean AND operations are executed pair-wise for each image and summed using an OR function.

Still another method does not require the use of a unique probe for each cell in the conjugate. Instead, a probe-free imaging modality such as brightfield (transmitted light) is used to image and mask the entire conjugate. If the conjugate consists of an antigen presenting cell and a T cell, only one of the two cell types need be probed. The mask of the probed cell image would then be subtracted from the mask of the brightfield image using a Boolean XOR function to define the mask of the unprobed cell. The synapse can then be defined much as in the previous example, by dilating either the unprobed or the probed cell mask, and combining it with its counterpart using the Boolean AND function. This methodology has the advantage over the previous methods of only requiring N−1 unique probes, where N is the number of different cell types to be distinguished in the conjugates under study.

The masking technique noted above will now be described in greater detail. The images of the over 10,000 objects (in this case, biological cells) initially imaged were first analyzed to identify a subpopulation of cell conjugates. The initial discrimination process identified an initial subpopulation of 1095 objects (i.e., cell conjugates) from the over 10,000 objects initially imaged. The subpopulation of cell conjugates was then further defined to include cell conjugates including a limited number of cells, and which include cells which are both in focus. In this manner, a subpopulation of 178 cell conjugates was selected from the 1095 objects included in the initial subpopulation. In terms of the imaging software employed, "User Modifications" were created in the "masks" for channels 3 (FITC) and 4 (PE), such that they tightly adhered to the boundary of the cell membrane, and defined for further use as "UM3" and UM4," respectively. Referring to FIG. 4, images in column 414 correspond to the FITC mask (UM3), while images in column 416 correspond to the PE mask (UM4).

Figure 6:
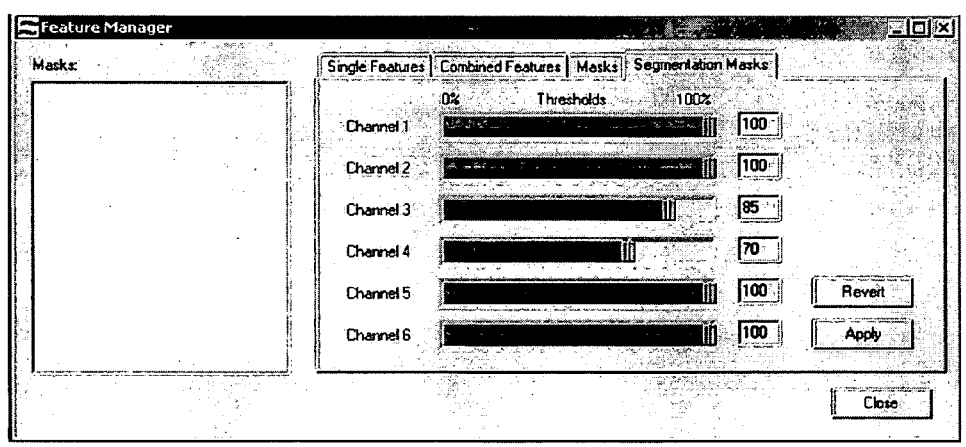
Figure 7:
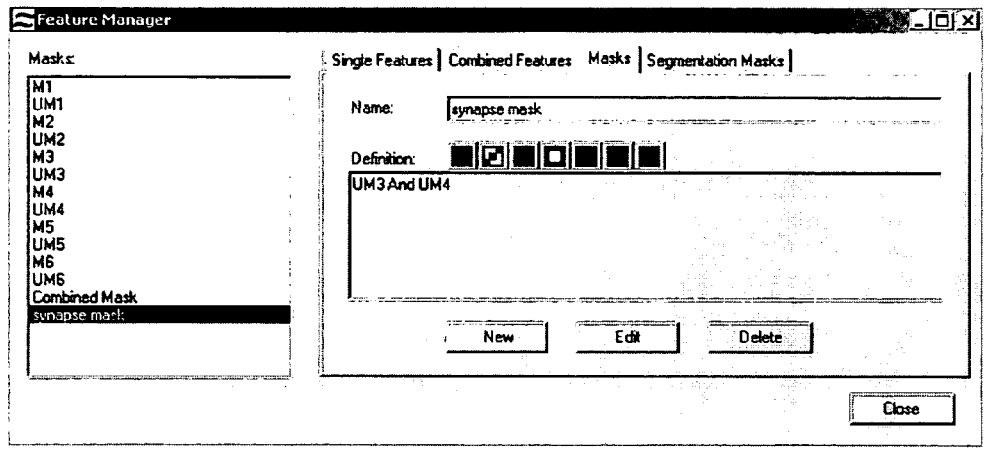

FIG. 6 is a screenshot of a graphical user interface from the exemplary image analysis software used to generate masks for Channels 3 and 4. FIG. 7 is a screenshot of a graphical user interface from the exemplary image analysis software used to generate a synapse mask using Boolean logic to combine the masks for Channels 3 and 4. Examples of the masks described, as well as brightfield and fluorescent images of the conjugates, are shown in FIG. 4.

Figure 8:
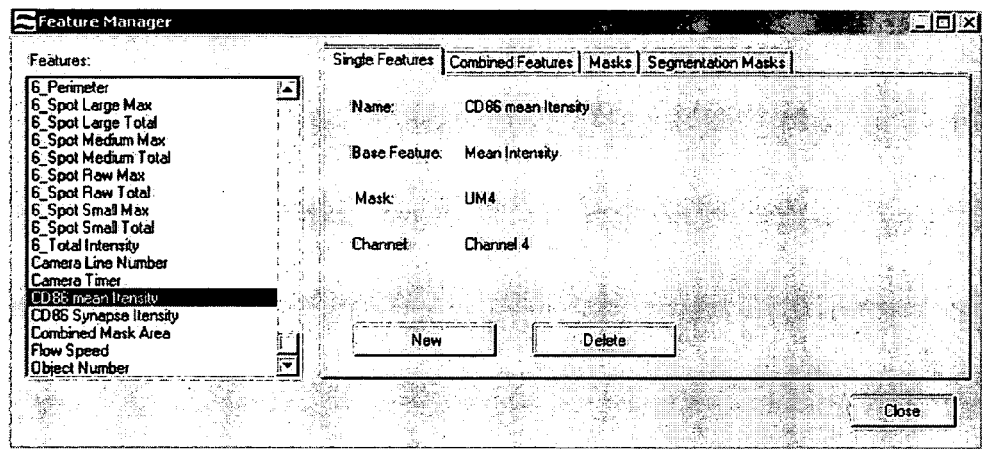
Figure 9:
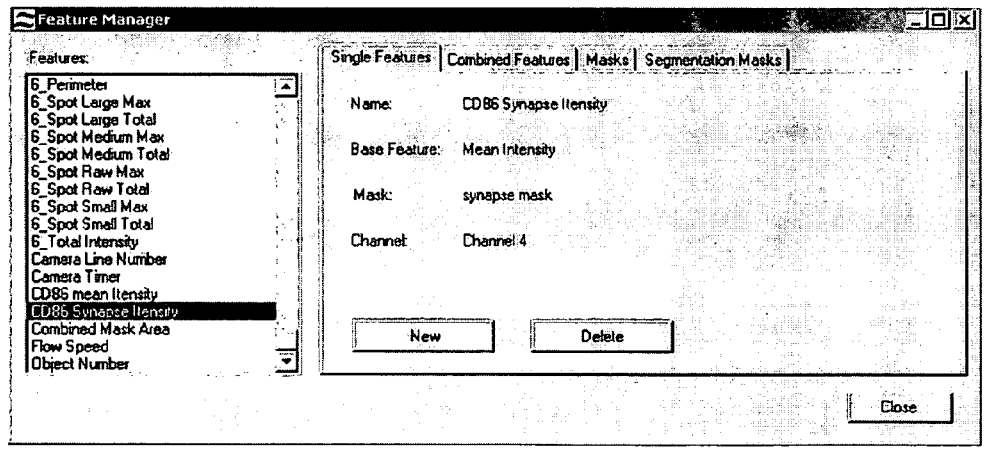

FIG. 8 is a screenshot of a graphical user interface from the exemplary image analysis software used to determine the mean signal intensities of CD86 in the entire antigen presenting cell (CD86 mean intensity), while FIG. 9 is a screenshot of a graphical user interface from the exemplary image analysis software used to determine the mean signal intensities of CD86 only within the interaction site (i.e., the synapse) between the T cell and the antigen presenting cell (CD86 Synapse Intensity).

Figure 10:
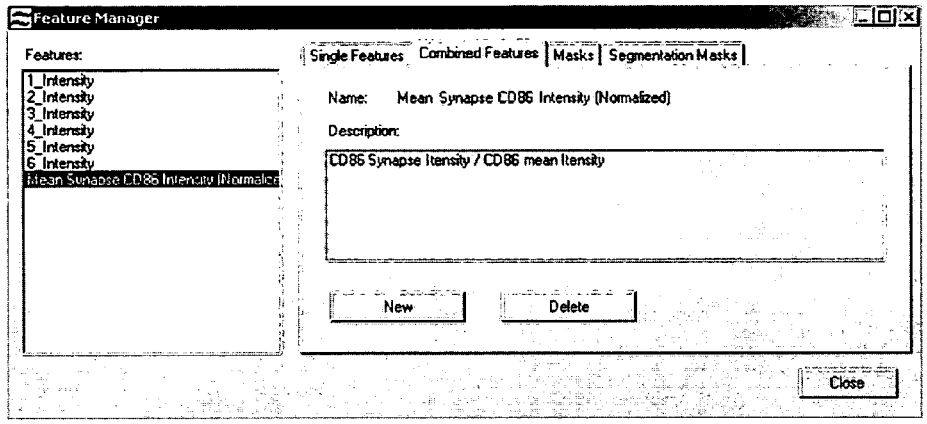

A complex feature was then created to normalize the signal intensity at the T cell/antigen presenting cell interface (i.e., at the synapse) by dividing the mean intensity of the CD86 signal at the synapse by the mean intensity of CD86 on the antigen presenting cell as a whole. FIG. 10 is a screenshot of a graphical user interface from the exemplary image analysis software used to normalize the signal intensity at the T cell/ antigen presenting cell interface. Using this approach, if there is significant redistribution of the molecule being measured (in this case CD86) to the synapse, the result of the calculation would be >1.0. In contrast, a number of <1.0 would be indicative of redistribution of the molecule in question away from the synapse. Finally, a calculated result approximating 1.0 would be indicative of no significant molecular redistribution on the cell membrane. The result of the empirical study is graphically illustrated in FIG. 11, which is a chart showing the frequency verses the mean synapse intensity of CD86.

A second, computer-assisted process was also used, in which the aspect ratio of the cells containing both red and green signals was determined to "objectify" identification of conjugates in which both cells were likely to be in the same focal plane. In this approach the "Aspect Ratio" of conjugates containing both T cells and antigen presenting cells was plotted. FIG. 12 is a chart showing the frequency of conjugates containing both T cells and antigen presenting cells.

Conjugates with a ratio approximating 0.9 (i.e., those cells with ratios between 0.8 and 1.0) were deemed likely to be conjugates in which the two cells were being viewed "end-on" relative to the objective lens, or conjugates of larger numbers of cells in a "ball" formation. This conjecture was verified by visual analysis of the gated subpopulation. FIG. 13 includes images of conjugates with a ratio approximating 0.9.

Conjugates with an aspect ratio approximating 0.3 (i.e., those cells with ratios between 0.2 and 0.4) were deemed likely to contain more than 2 cells per conjugate, and thus also to have a greater probability of containing cells that were out of focus. This conjecture was also verified by visual analysis of the gated subpopulation. FIG. 14 includes images of conjugates with a ratio approximating 0.3.

Conjugates with an aspect ratio approximating 0.5 (range between 0.4 and 0.6) were considered most likely to contain the highest proportion of 2 cells per conjugate, an expectation that was also verified by visual inspection of the data. FIG. 15 includes images of conjugates with a ratio approximating 0.5.

Calculation of the Mean Synapse CD86 Intensity (Normalized) was also performed, and also revealed a value of approximately 1.0 (consistent with the value determined using the mask based technique discussed above). FIG. 16 is a chart showing frequency verses the mean synapse intensity of CD86 for conjugates with an aspect ratio approximating 0.5.

Next a "Focus Gate" was imposed on the cells with an aspect ratio of 0.5, and the subpopulation of cells considered to be in reasonably good focus (i.e., those cells with a "Gradient Max" value in the brightfield channel of >0.5) were evaluated. FIG. 17 is a chart showing the frequency of cell conjugates considered to be in reasonably good focus.

Calculation of the Mean Synapse CD86 Intensity (Normalized) was performed, and also revealed a value of approximately 1.0. FIG. 18 is a chart showing frequency verses the normalized mean synapse intensity of CD86.

Exemplary Computing Environment

As noted above, an aspect of the present invention involves image analysis of a plurality of images simultaneously collected from members of the population of objects. Reference has been made to an exemplary image analysis software package. FIG. 19 and the following related discussion are intended to provide a brief, general description of a suitable computing environment for practicing the present invention, where the image processing required is implemented using a computing device functionally related to that shown in FIG. 19. Those skilled in the art will appreciate that the required image processing may be implemented by many different types of computing devices, including a laptop and other portable computers, multiprocessor systems, networked computers, mainframe computers, hand-held computers, personal data assistants (PDAs), and on other types of computing devices that include a processor and a memory for storing machine instructions, which when implemented by the processor, result in the execution of a plurality of functions.

An exemplary computing system 150 suitable for implementing the image processing required in the present invention includes a processing unit 154 that is functionally coupled to an input device 152, and an output device 162, e.g., a display. Processing unit 154 include a central processing unit (CPU 158) that executes machine instructions comprising an image processing/image analysis program for implementing the functions of the present invention (analyzing a plurality of images simultaneously collected for members of a population of objects to enable at least one characteristic exhibited by members of the population to be measured). In at least one embodiment, the machine instructions implement functions generally consistent with those described above, with reference to the flowchart of FIG. 3, as well as the exemplary screenshots. Those of ordinary skill in the art will recognize that CPUs suitable for this purpose are available from Intel Corporation, AMD Corporation, Motorola Corporation, and other sources.

Also included in processing unit 154 are a random access memory 156 (RAM) and non-volatile memory 160, which typically includes read only memory (ROM) and some form of memory storage, such as a hard drive, optical drive, etc. These memory devices are bi-directionally coupled to CPU 158. Such storage devices are well known in the art. Machine instructions and data are temporarily loaded into RAM 156 from non-volatile memory 160. Also stored in memory are the operating system software and ancillary software. While not separately shown, it should be understood that a power supply is required to provide the electrical power needed to energize computing system 150.

Input device 152 can be any device or mechanism that allows input into the operating environment. This includes, but is not limited to a mouse, keyboard, microphone, modem, pointing, or other input devices. While not specifically shown in FIG. 19, it should be understood that computing system 150 is logically coupled to an imaging system such as that schematically illustrated in FIG. 1, such that the image data collected is available to computing system 150 to achieve the desired image processing. Of course, rather than logically coupling the computing system directly to the imaging system, data collected by the imaging system can simply be transferred to the computing system by means of many different data transfer devices, such as portable memory media. Output device 162 will most typically comprise a monitor or computer display designed for human perception of output.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for determining one or more characteristics of a subpopulation of objects from images collected from a population of objects, comprising the steps of:
   (a) imaging the population of objects to collect image data, while there is relative movement between the population of objects and an imaging system used to image the population of objects, where each object in the population of objects is imaged using the following steps:
      (i) dispersing light from the object into a plurality of light beams;
      (ii) focusing the plurality of light beams to produce respective images, each respective image corresponding to a different one of the plurality of light beams; and
      (iii) providing a time delay integration (TDI) detector disposed to receive the respective images, the steps of dispersing the light and providing the TDI detector being implemented such that the dispersed light is dispersed across the detector in a direction that is substantially orthogonal to a direction of a motion of the respective images across the TDI detector, enabling a plurality of different images of the object to be acquired simultaneously;
   (b) using the image data to define the subpopulation of objects, the subpopulation of objects being encompassed by the population of objects;
   (c) identifying an object feature exhibited by the subpopulation of objects; and
   (d) using the image data to measure at least one characteristic associated with the object feature.

2. The method of claim 1, wherein the step of simultaneously collecting a plurality of images for each object in the population of objects comprises the step of simultaneously collecting at least two of the following types of images: a brightfield image, a darkfield image, and a fluorescent image.

3. The method of claim 1, wherein the population of objects comprises at least two different types of objects.

4. The method of claim 3, wherein before the population of objects is imaged, further comprising the step of labeling at least one of the at least two different types of objects.

5. The method of claim 3, wherein the objects comprise biological cells.

6. The method of claim 3, wherein the population of objects comprise T cells and antigen presenting cells.

7. The method of claim 3, wherein the step of using the image data to define the subpopulation of objects comprises a step of defining the subpopulation to comprise conjugated cells.

8. The method of claim 7, wherein the step of identifying the object feature exhibited by the subpopulation of objects comprises the step of identifying a synapse between the conjugated cells.

9. A method for determining one or more characteristics of a subpopulation of objects from images collected from a population of objects, comprising the steps of:
   (a) imaging the population of objects to collect image data, while there is relative movement between the population of objects and an imaging system used to image the population of objects, such that a plurality of images for individual objects in the population of objects are simultaneously collected, the plurality of images comprising at least two of the following types of images: a brightfield image, a darkfield image, and a fluorescent image;
   (b) using the image data to define the subpopulation of objects, the subpopulation of objects being encompassed by the population of objects;
   (c) identifying an object feature exhibited by the subpopulation of objects; and
   (d) using the image data to measure at least one characteristic associated with the object feature.

10. The method of claim 9, wherein before the population of objects is imaged, further comprising the step of labeling a plurality of individual objects encompassed by the population of objects.

11. The method of claim 9, wherein the population of objects comprises at least two different types of objects.

12. The method of claim 11, wherein before the population of objects is imaged, further comprising the step of labeling at least one of the at least two different types of objects.

13. The method of claim 11, wherein the population of objects comprise T cells and antigen presenting cells.

14. The method of claim 11, wherein the step of using the image data to define the subpopulation of objects comprises a step of defining the subpopulation to comprise conjugated cells.

15. The method of claim 11, wherein the step of identifying the object feature exhibited by the subpopulation of objects comprises the step of identifying a synapse between the conjugated cells.

16. The method of claim 9, wherein each individual object in the population of objects is imaged using the following steps:
   (a) dispersing light from the object into a plurality of light beams;
   (b) focusing the plurality of light beams to produce respective images, each different respective image corresponding to one of the plurality of light beams; and
   (c) providing a time delay integration (TDI) detector disposed to receive the respective images, the steps of dispersing the light and providing the TDI detector being implemented such that the dispersed light is dispersed across the detector in a direction that is substantially orthogonal to a direction of a motion of the respective images across the TDI detector.

17. A method for determining one or more characteristics shared by a group of objects, comprising the steps of:

(a) imaging a population of objects to collect image data, while there is relative movement between the population of objects and an imaging system used to image the population of objects, such that a plurality of images for individual objects in the population of objects are simultaneously collected, such that the plurality of images for an individual object are not optically combined when they are collected;

(b) identifying an object feature exhibited by a group of objects encompassed in the population of objects; and (c) using the image data to measure at least one characteristic associated with the object feature.

18. The method of claim 17, wherein each individual object in the population of objects is imaged using the following steps:

(a) dispersing light from the object into a plurality of light beams;

(b) focusing the plurality of light beams to produce respective images, each respective image corresponding to a different one of the plurality of light beams; and (c) providing a time delay integration (TDI) detector disposed to receive the respective images, the steps of dispersing the light and providing the TDI detector being implemented such that the dispersed light is dispersed across the detector in a direction that is substantially orthogonal to a direction of a motion of the respective images across the TDI detector.

19. A method for determining one or more characteristics of a subpopulation of objects from images collected from a population of objects, comprising the steps of:

(a) imaging the population of objects to collect image data, while there is relative movement between the population of objects and an imaging system used to image the population of objects, such that for each object, a plurality of individual images are simultaneously collected;

(b) using the image data to define the subpopulation of objects, the subpopulation of objects being encompassed by the population of objects;

(c) identifying an object feature exhibited by the subpopulation of objects; and (d) using the image data to measure at least one characteristic associated with the object feature.

* * * * *